(12) United States Patent
Tsukii et al.

(10) Patent No.: US 7,957,002 B2
(45) Date of Patent: Jun. 7, 2011

(54) METHOD FOR OPTICAL MEASUREMENT AND OPTICAL MEASUREMENT APPARATUS

(75) Inventors: Ken Tsukii, Tokyo (JP); Jie Xu, Tokyo (JP); Kenichi Kimura, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 222 days.

(21) Appl. No.: 12/403,772

(22) Filed: Mar. 13, 2009

(65) Prior Publication Data

US 2010/0231913 A1 Sep. 16, 2010

(51) Int. Cl.
*G01N 21/00* (2006.01)
(52) U.S. Cl. .......................... 356/436; 356/441; 356/442
(58) Field of Classification Search ........... 356/432–444
See application file for complete search history.

(56) References Cited

U.S. PATENT DOCUMENTS

| | | | | |
|---|---|---|---|---|
| 4,125,769 A | * | 11/1978 | Marten et al. | 378/47 |
| 4,265,538 A | * | 5/1981 | Wertheimer | 356/246 |
| 4,660,971 A | * | 4/1987 | Sage et al. | 356/39 |
| 4,728,190 A | * | 3/1988 | Knollenberg | 356/336 |
| 5,312,535 A | | 5/1994 | Waska et al. | |
| 5,414,508 A | * | 5/1995 | Takahashi et al. | 356/246 |
| 6,120,734 A | * | 9/2000 | Lackie | 422/68.1 |
| 6,573,992 B1 | * | 6/2003 | Drake | 356/338 |
| 7,108,400 B2 | * | 9/2006 | Yamada et al. | 362/294 |
| 7,151,604 B2 | * | 12/2006 | Saccomanno et al. | 356/343 |
| 2009/0021722 A1 | | 1/2009 | Tsukii et al. | |
| 2009/0032731 A1 | | 2/2009 | Kimura et al. | |

FOREIGN PATENT DOCUMENTS

JP 2973387 9/1999

* cited by examiner

*Primary Examiner* — Gregory J Toatley
*Assistant Examiner* — Jarreas C Underwood
(74) *Attorney, Agent, or Firm* — Oblon, Spivak, McClelland, Maier & Neustadt, L.L.P.

(57) ABSTRACT

An optical measurement apparatus can be provided, in which the sample is optically measured without loss of the illuminating light with high sensitivity. A glass plate as the transparent member 50 is placed in the interface between the end face 43 of the optical waveguide 40 guiding the illuminating light L generated by the laser light source 20 and the wall face of the capillary 30. According to the above feature, the air layer is prevented from existing in the interface between the end face 43 of the optical fiber 40 and the wall face of the capillary 30, thus the sample S can be optically measured with high sensitivity and few variability without causing the loss of the illuminating light L.

5 Claims, 2 Drawing Sheets

METHOD FOR OPTICAL MEASUREMENT AND OPTICAL MEASUREMENT APPARATUS

BACKGROUND OF THE INVENTION

1. Field of the Invention

The present invention relates to an optical measurement apparatus, in particular to an optical measurement apparatus in which an illuminating light is irradiated to the sample in order to measure optical information of the sample dispersed in the liquid flowing through the flow passage.

2. Description of the Related Art

It is proposed that optical information (fluorescent information) of the sample in the liquid flow is measured in which the liquid with the sample dispersed therein flows in the capillary and the light from the light source is irradiated to the liquid flow (refer to Japanese Patent No. 2973387).

In the measurement apparatus disclosed in the Japanese Patent No. 2973387, a laser light is irradiated through the optical fiber to the sample passing through the capillary. However, the end face of the optical fiber is placed in close to the surface of the capillary. Accordingly, the air layer is formed in the interface between the end face of the optical fiber and the surface of the capillary.

Since the refractive indexes in the optical fiber to the air layer, and the air layer to the capillary are different, the optical loss of the irradiated light from the end face of the optical fiber to the capillary is caused to make it difficult to measure the sampling with high sensitivity.

Measured value dispersion varies depending on the irradiated area to the range of the flowing sample, the adjustment in the interrelation is important.

One of the object of the invention is to provide an optical measurement apparatus, for overcoming the above described problems, in which the sample is optically measured without loss of the illuminating light with high sensitivity so as to reduce variability in measurement.

SUMMARY OF THE INVENTION

In order to solve the above described problems, the optical optical measurement apparatus comprises the apparatus in which an illuminating light is irradiated to a sample in order to measure optical information of the sample dispersed in a liquid flowing through a flow passage, wherein a transparent member is arranged in an interface between an end face of an optical waveguide guiding the illuminating light generated by a light source and a wall face of the flow passage.

In the optical measurement apparatus, the optical waveguide preferably comprises an optical fiber.

In the optical measurement apparatus, the transparent member preferably comprises glass.

In the optical measurement apparatus, a wall face to the flow passage side of the transparent member preferably directly contacts with the flow passage.

In the optical measurement apparatus, a refractive index matching agent for matching an optical refractive index is preferably placed in each interface between the end face of the optical waveguide and the transparent member, and between the transparent member and the wall face of the flow passage.

In the optical measurement apparatus, a refractive index matching agent for matching an optical refractive index is preferably placed in an interface between the end face of the optical waveguide and the transparent member.

In the optical measurement apparatus, the refractive index matching agent placed in the interface between the end face of the optical waveguide and the transparent member preferably comprises a low-viscosity refractive index matching agent, and a high-viscosity refractive index matching agent is placed surrounding the low-viscosity refractive index matching agent.

In the optical measurement apparatus, the optical waveguide is preferably supported movably along an axis direction of the optical waveguide, a first direction perpendicular to the axis direction of the optical waveguide, and a second direction respectively perpendicular to the axis direction of the optical waveguide and the first direction.

In the optical measurement apparatus, a plurality of the optical waveguides are preferably arranged along the flow passage, and supported movably in block.

DETAILED DESCRIPTION OF THE INVENTION

Preferable embodiments of the invention are described in detail with reference to the drawings.

Figure 1:
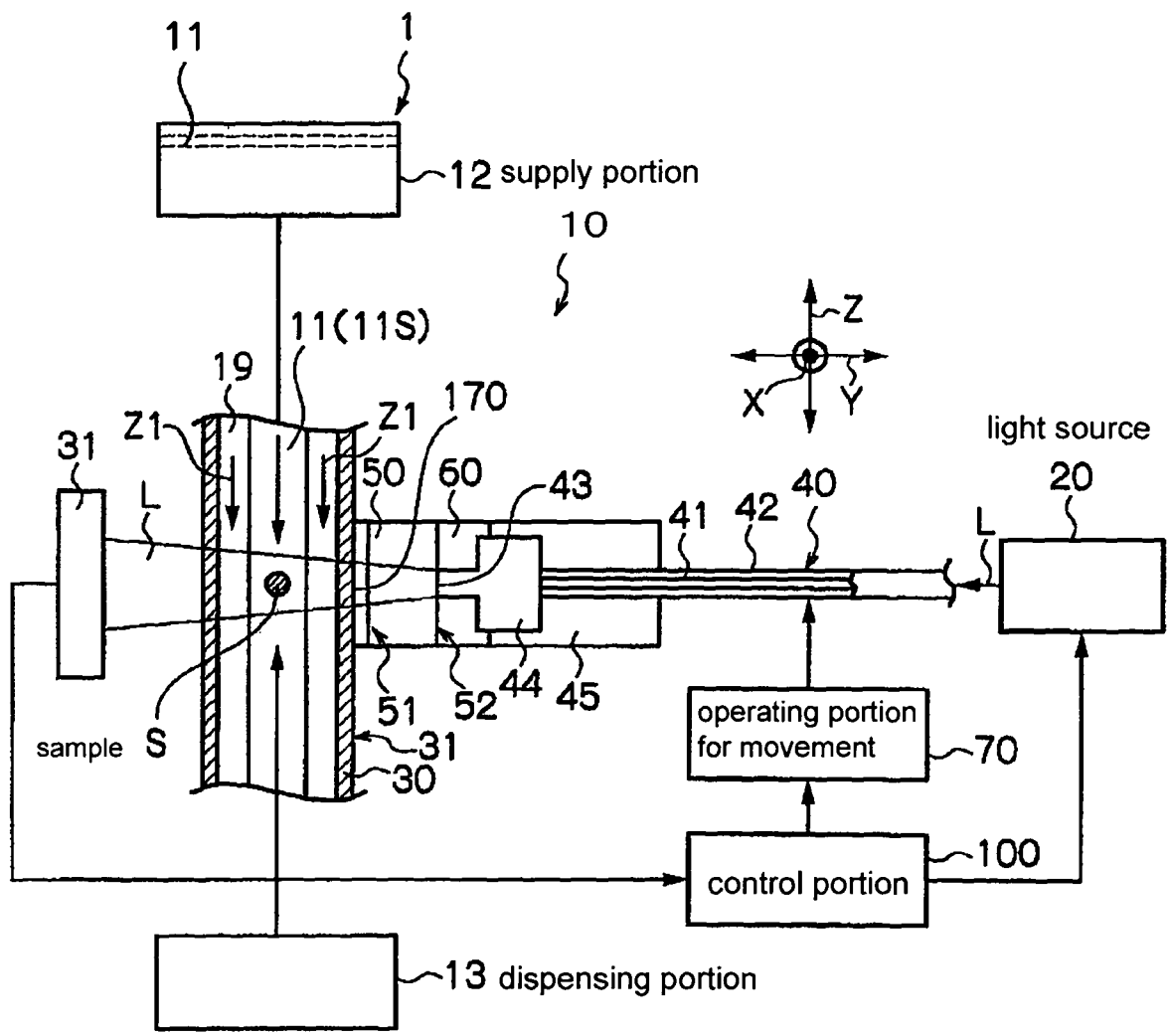
FIG. 1 is a perspective view showing an example of a flow cyto meter including a preferable embodiment of the optical measurement apparatus of the invention.
Figure 2:
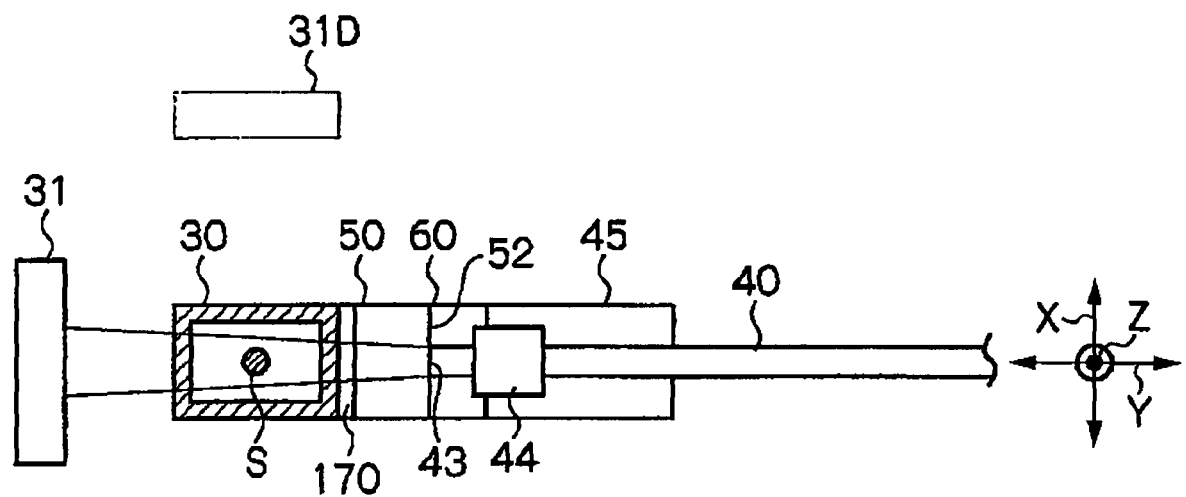
FIG. 2 is a plan view of the optical measurement apparatus depicted in FIG. 1.

FIGS. 1 and 2 depict a preferable embodiment of an optical measurement apparatus of the invention. An example of the configuration of the optical measurement apparatus 1 of the invention depicted in FIGS. 1 and 2 is described.

The optical measurement apparatus 10 depicted in FIG. 1 is utilized as an optical measurement portion in the flow cyto meter (or may called as flow cyto metry), for example. The flow cyto meter 1 includes the optical measurement apparatus 10, a supply portion 12 for supplying liquid in which a sample is dispersed, and a dispensing portion 13 for dispensing the sample.

The supply portion 12 can supply the liquid 11 with the sample S dispersed through a tube 14 as the sample flow 11S together with a sheath flow 19 in a Z1 direction to the optical measurement apparatus 10 (from the upper side to the down side in the example in FIG. 1). The sample S in the liquid passing through the optical measurement apparatus 10 can be divided into necessary substance and unnecessary substance in the dispensing portion 13.

The optical measurement apparatus 10 depicted in FIG. 1 includes a laser light source 20 for example as a light source of an illuminating light L, a capillary as a flow passage for flowing a sample flow 11S including the sample S, a light receiving portion 31, an optical fiber 40 as a waveguide for guiding the illuminating light L, a glass plate 50, a matching oil 60, an operating portion 70 for movement, and a control portion 100. The light receiving portion comprises a photodiode, for example.

The optical measurement apparatus 10 is the apparatus for measuring an optical information (fluorescent information) of the sample obtained by irradiating the illuminating light (irradiating light) L generated by the laser light source 20 to the sample S in the sample flow (liquid) 11S passing through the capillary 30. The liquid 11 in the supply portion 12 is supplied in the capillary along the Z1 direction together with the sheath flow 19 as the sample flow (liquid).

The sample S depicted in FIGS. 1 and 2 comprises a cell having 5 μm diameter for example. The sample flow 11S is passed through the capillary 30 of the optical measurement apparatus 10 in such configuration that the sample flow 11S is encompassed (surrounded) by the sheath flow 19.

The sheath flow technology using the sheath flow 19 arbitrarily controls the width of the sample flow 11S by the pressure difference between the sample flow 11S and the sheath flow 19 so as to reduce pressure drop of the sample flow 11S and to prevent from clogging.

As depicted in FIG. 1, the illuminating light from the laser light source 20 is irradiated to the sample S in the supplied sample flow 11S through the optical fiber 40, the matching oil 60, the glass plate 50 and the outer face 31F of the transparent wall portion of the capillary 30. The illuminating light L irradiated to the sample S is received by the light receiving portion 31, and the fluorescent information generated by the sample S is obtained. The obtained fluorescent information is forwarded to the control portion 100, thus fluorescent measuring value is analyzed in the control portion 100.

The optical fiber 40 has a core 41 and a cladding 42 surrounding the core 41 as a structure, as depicted in FIG. 1. An optical connector 44 is attached on the end face 43 of the optical fiber 40. The optical connector 44 is supported by a holder 45.

The capillary 30 depicted in FIGS. 1 and 2 is made of glass, for example. The glass plate 50 is a transparent intermediate member placed between the outer face 31F of the wall face of the capillary 30 and the end face 43 of the optical fiber 40. Thus an air layer is not allowed to exist between the other face 52 of the glass plate 50 and the end face 43 of the optical fiber 40. The end face 43 of the optical fiber 40 and the other face 52 of the glass plate 50 are preferably positioned on the same plane.

Furthermore, a matching oil 60 is filled in the interface between the other face 52 of the glass plate 50 and the end face of the optical connector 44, namely the end face 43 of the optical fiber 40. The matching oil is a refractive index matching agent to match the optical refractive index of the glass plate 50 with the optical refractive index of the optical fiber 40, while the air layer is not allowed to exist between the other face 52 of the glass plate 50 and the end face 43 of the optical fiber 40. The matching oil is transparent oil which can pass the illuminating light.

In the same manner, a refractive index matching agent 170 such as the matching oil is preferably placed between the one face 51 of the glass plate 50 and the outer face 31 of the wall face of the capillary 30.

As depicted in FIG. 1, the optical fiber is movable in the X axis direction, Y axis direction and Z axis direction by the action of the operating portion 70 for movement. The action of the operating portion 70 for movement is controlled by the instruction from the control portion 100. 3 axes trolley table such as generally used X-Y-Z table is utilized as the operating portion 70 for movement.

The operating portion 70 for movement is an adjustment mechanism for adjusting the position of the illuminating light L to the sampling flow 11S. X axis, Y axis and Z axis are perpendicular each other. The respective center positions of the illuminating light L and the sample flow 11S can be adjusted by adjusting the position of the optical fiber along the X axis. The diameter of irradiation of the illuminating light L can be adjusted by adjusting the position of the optical fiber 40 along the Y axis. The position of the optical axis can be adjusted to the optical fiber in the side of light receiving portion 31 by adjusting the position of the optical fiber along the X axis. The Y axis is identical to the axis direction of the optical fiber 40. The X axis direction and the Y axis direction are respectively the first direction and the second direction perpendicular to the Y axis direction.

According to the above, it is possible to expand the illuminating light L so as to irradiate corresponding to the size of the sample S, and the position of the sample S passing through the capillary 30, without allowing the air layer exist in the interface between the other face 52 of the glass plate 50 and the end face 43 of the optical fiber 40. The irradiating area can be adjusted while the irradiating diameter, irradiating density, and numerical aperture of the illuminating light L are varied.

Then, an operational example of the optical measurement apparatus depicted in FIG. 1 is described.

When the liquid 11 is supplied within the capillary 30 using the sheath flow 19 in the Z1 direction as the sample flow 11S from the supply portion 12, the fluorescent information of the sample S is obtained by the illuminating light L in the optical measurement apparatus 10 and received in the light receiving portion 31.

On this occasion, the illuminating light L of the laser light source 20 passes through the optical fiber 40 where the matching of the refractive index is implemented by the matching oil 60, and passes the glass plate 50 and the wall portion of the capillary to be irradiated into the sample S. The matching oil 60 can match the refractive index of the optical fiber 40 with the refractive index of the glass plate 50.

Furthermore, since one face 51 of the glass plate 50 is attached tightly to the outer face 31F of the wall portion of the capillary 30, and the matching oil 60 is filled in the interface between the other face 52 of the glass plate 50 and the end face of the optical connector, i.e., the end face 43 of the optical fiber 40, it is possible not to allow the air layer to exist in the interface between the outer face 31F of the wall portion of the capillary 30 and the end face 43 of the optical fiber 40. Thus, the loss of the illuminating light L due to the existing of the air layer does not occur.

In addition, since the matching oil is filled in the interface between the other face 52 of the glass plate 50 and the end face of the optical connector, namely the end face 43 of the optical fiber 40, even if the optical fiber is moved in at least one direction of the X axis direction, Y axis direction and Z axis direction by means of the operating portion 70 for movement, the end face 43 of the optical fiber 40 can move within the matching oil 60, so that the air layer is not allowed to exist in the interface between the outer face of the wall portion of the capillary 30 and the end face 43 of the optical fiber 40, thus the fluorescent information of the sample S can be optically measured with high sensitivity.

Furthermore, since the end face 43 of the optical fiber 40 is not configured to be directly placed face to face with the wall portion of the capillary 30, the end face 43 of the optical fiber can be prevented from being damaged.

As described above, according to the optical measurement apparatus 10 of the present invention, the precise optical measurement of the sample can be implemented with high sensitivity without losing the illuminating light.

If the air layer exists in the interface between the outer face of the wall portion of the capillary 30 and the end face 43 of the optical fiber 40, 4% of loss may be caused in the illuminating light, for example.

Figure 3:
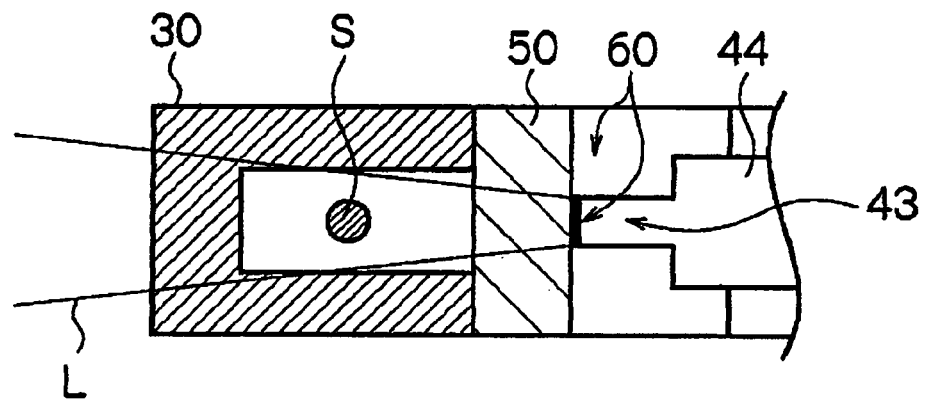
FIG. 3 is a plan view showing another embodiment of the invention.

FIG. 3 shows another embodiment of the present invention in which the transparent member 50 is configured to be one of the flow passage wall of the capillary 30 as an example. The transparent member 50 is placed outside of the outer face of the flow passage wall of the capillary 30 in the embodiment depicted in FIGS. 1 and 2, so that the transparent member 50 is placed outside of the flow passage. Contrary to the above, the inner wall of the transparent member 50 is configured to form the inner wall face of the flow passage.

The optical measurement apparatus 10 is the apparatus in which the light is irradiated into the sample as an object to be measured, dispersed in the liquid flowing through the flow passage to measure the optical information of the sample. The transparent member 50 is placed in the interface between the end face 43 of the optical waveguide 40 guiding the illuminating light L generated by the laser light source 20 and the wall face of the capillary 30 as the flow passage. According to the above feature, the air layer is prevented from existing in the interface between the end face 43 of the optical fiber 40 and the wall face of the capillary 30, thus the sample S can be optically measured with high sensitivity and few variability without causing the loss of the illuminating light L.

In the embodiment of the invention, the transparent member 50 comprises glass. Since the generally used material for the transparent member 50 is utilized, a lower cost thereof can be possible. In addition, it is possible to adjust the diameter of the irradiation of the illuminating light, as well as the position thereof.

In the embodiment of the present invention, the wall face 51 positioned in the flow passage side of the transparent member 50 contact directly with the flow passage. According to the above feature, the transparent member 50 can be placed in the interface between the end face 43 of the optical fiber 40 and the flow passage by a simple configuration. Since the refractive index matching agent is placed only in the interface between the wall face 51 in the flow passage side and the transparent member 50, the necessary number of the transparent member is one, so that the necessary number of the refractive index matching agent to be placed is only one.

In the embodiment of the present invention, the refractive index matching agent for matching the refractive index of the light is placed respectively in the interface between the end face 43 of the optical waveguide and the transparent member 50, as well as in the interface between the transparent member 50 and the wall face 31 of the flow passage, thus enabling to reduce the optical loss of the irradiating light L.

In the embodiment of the present invention, the refractive index matching agent for matching the refractive index of the light is placed in the interface between the end face 43 of the optical waveguide and the transparent member 50, thus enabling to reduce the optical loss of the irradiating light L.

In the embodiment of the present invention, the refractive index matching agent in the interface between the end face 43 of the optical waveguide and the transparent member 50 is formed by a low-viscosity refractive index matching agent and a high-viscosity refractive index matching agent surrounding the low-viscosity refractive index matching agent. Accordingly, the transparent member 50 can be supported with the use of the high-viscosity refractive index matching agent, while the transparent member 50 cannot be supported only with the use of the low-viscosity refractive index matching agent. Furthermore, since the high-viscosity refractive index matching agent into which air bubble easily infiltrates is placed surrounding the low-viscosity refractive index matching agent, the irradiation of the irradiating light L is not affected even if the air bubble infiltrates therein.

In the optical measurement apparatus 10 of the invention, the optical fiber 40 is supported movably along the axis direction (Y axis direction) of the optical fiber 40, the first direction (X axis direction) perpendicular to the Y axis direction, and the second direction (Z axis direction) perpendicular to the respective Y axis direction and X axis direction. According to the above feature, the illuminating light L is expanded to irradiate in corresponding to the size of the sample S and the position through which the sample flows in the capillary 30. Thus, the irradiating diameter, irradiating density, and the numerical aperture of the illuminating light can be varied so as to adjust the irradiating range.

In the embodiment of the present invention, a plurality of optical waveguides are arranged along the flow passage, and the optical waveguides are movably supported as in block. Thus, the positions of the end faces of the plurality of optical fibers can be adjusted with high precision at the same time.

In the embodiment of the present invention, the irradiating diameter of the irradiating light L can be adjusted by varying the thickness of the transparent member 50. The diameter of the sample flow is different in the object to be measured. However the adjusting range is limited because it has the configuration in which the refractive index matching agent is introduced in the adjustment of the position of the end face. So, it is configured that the irradiating diameter of the irradiating light L is adjusted depending on the diameter of the sample flow by the thickness of the transparent member, thus it is possible to correspond to the various samples.

It can also be configured to use the optical fiber while the transparent member 50 is placed outside as a capillary (glass tube).

The optical loss of the irradiating light L can be reduced with the use of the refractive index matching agent.

Furthermore, the foreign substance such as dust can be prevented from adhering to the end face of the optical fiber as the optical waveguide (the foreign substance is burned by the heat energy). Accordingly, the end face of the optical fiber can be effectively prevented from being damaged.

Two kinds of refractive index matching agents are used. It is difficult to support with the use of the low-viscosity refractive index matching agent, while air bubble can be easily mixed with the use of high-viscosity refractive index matching agent upon moving and setting up. When the low-viscosity refractive index matching agent is placed on the end face of the optical fiber and the high-viscosity refractive index matching agent is placed surrounding the low-viscosity refractive index matching agent, it can be configured that it is possible to be supported and the air bubble can be effectively prevented from infiltrating.

It is configured that the end faces of the optical fibers are arranged along the flow passage, and movably supported as in block. Thus, the positions of the end faces of the plurality of optical fibers can be adjusted with high precision at the same time. It may be configured that optical multi-fiber connector is used as the plurality of optical fibers.

The present invention can be applied to the various modifications without being limited to the above described embodiments.

For example, although the light receiving portion 31 depicted in FIG. 1 is placed opposite to the glass plate 50, which sandwiches the capillary 30, the light receiving portion 31D may be arranged in the position lateral to the capillary 30 (the position along the perpendicular to the plane of paper in FIG. 1) as depicted in FIG. 2 without being limited to the above.

Although the capillary 30 depicted in FIGS. 1 and 2 is a hollow member having a cross section of square for example, the capillary may have the cross section of rectangle or other shape for example.

The optical signal such as scattered light and the transmitted light obtained by the cell as the sample, for example, and the fluorescent information can be obtained with the use of the light receiving portion 31.

Other material such as plastic plate as far as the transparency is concerned may be used as the transparent member, without being limited to the glass plate.

In the present invention, the illuminating light may be called as a measuring light or irradiating light.

The optical measurement apparatus of the invention is applicable to such various fields as the field in which examination, analysis and break down is required concerning such biological polymer as gene, immune system, protein tyrosine, amino acid, sugar group, for example, engineering field, general agronomy such as food, agricultural commodity, sea food processing or the like, pharmaceutical field, medicine field such as sanitation, health, immune, epidemic, heredity or the like, science field such as chemistry, biology or the like.

According to the optical measurement apparatus of the invention, the sample can be optically measured without loss of the illuminating light with high sensitivity so as to reduce variability in measurement.

What is claimed is:

1. An optical measurement apparatus in which an illuminating light is irradiated to a sample in order to measure optical information of the sample dispersed in a liquid flowing through a flow passage,
    wherein a transparent member is arranged in an interface between an end face of an optical waveguide guiding the illuminating light generated by a light source and a wall face of the flow passage,
    wherein the transparent member comprises glass,
    wherein a wall face to the flow passage side of the transparent member directly contacts with the flow passage,
    wherein the refractive index matching agent placed in the interface between the end face of the optical waveguide and the transparent member comprises a low-viscosity refractive index matching agent, and a high-viscosity refractive index matching agent is placed surrounding the low-viscosity refractive index matching agent,
    wherein the optical waveguide is supported movably along an axis direction of the optical waveguide, a first direction perpendicular to the axis direction of the optical waveguide, and a second direction respectively perpendicular to the axis direction of the optical waveguide and the first direction.

2. The optical measurement apparatus according to claim 1, wherein the optical waveguide comprises an optical fiber.

3. The optical measurement apparatus according to claim 1, wherein a refractive index matching agent for matching an optical refractive index is placed in each interface between the end face of the optical waveguide and the transparent member, and between the transparent member and the wall face of the flow passage.

4. The optical measurement apparatus according to claim 1, wherein a refractive index matching agent for matching an optical refractive index is placed in an interface between the end face of the optical waveguide and the transparent member.

5. The optical measurement apparatus according to claim 1, wherein a plurality of the optical waveguides are arranged along the flow passage, and supported movably in block.

* * * * *